BEST AVAILABLE COPY
Filed June 14
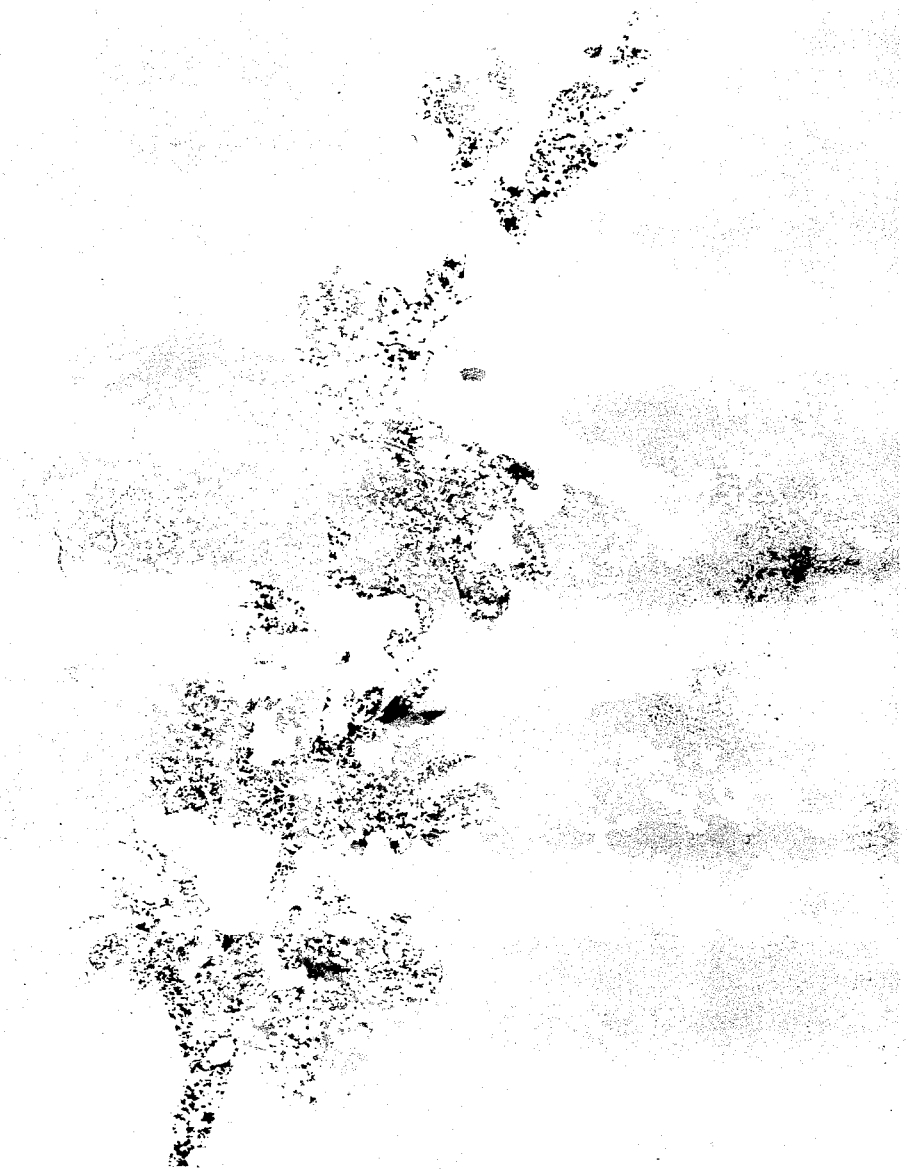
Inventor.
H. C. Swim
By Robert Ball
Atty.

BEST AVAILABLE COPY
July 24, 1951 H. C. SWIM Plant Pat. 1,022
COMBINED ORNAMENTAL AND FRUITING PEACH TREE
Filed June 14, 19 2 Sheets-Sheet 2
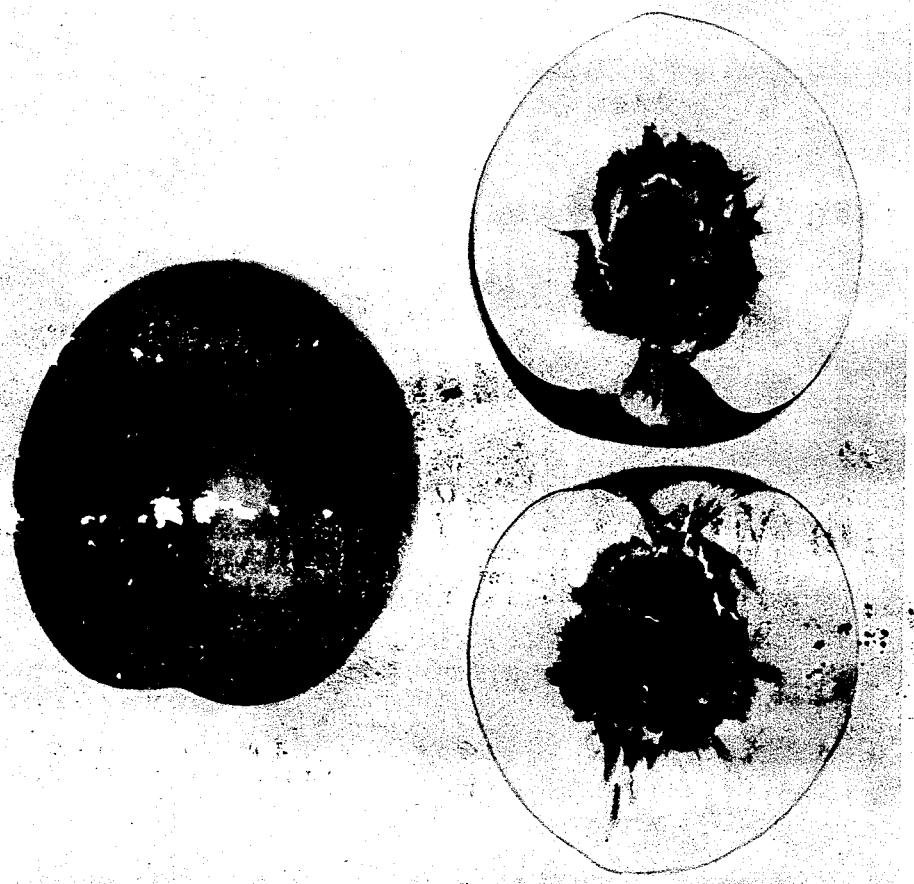
Inventor.
H. C. Swim
By: Robert Cobb
Attorneys.

BEST AVAILABLE COPY

Patented July 24, 1951

Plant Pat. 1,022

UNITED STATES PATENT OFFICE 1,022

COMBINED ORNAMENTAL AND FRUITING PEACH TREE

Herbert C. Swim, Ontario, Calif., assignor to Armstrong Nurseries, Inc., Ontario, Calif., a corporation of California Application June 14, 1950, Serial No. 167,939

1 Claim. (Cl. 47—62)

The present invention relates to a new and distinct variety of peach tree, originated from seed resulting from hand pollination of a seedling of "Swatow" peach (unpatented) × "Rio Oso Gem" peach (Plant Patent No 84), with pollen from an unnamed seedling resulting from a cross of "Babcock" peach (unpatented) × an unnamed seedling of "Babcock" peach × "Swatow" peach.

In points of novelty and distinctiveness, the above noted breeding has produced a peach tree, the characteristics of which are unlike any other known variety in commerce today, and the combination of these characteristics makes this new variety stand out from all others in the following important respects:

(1) The new variety bears white-fleshed, freestone fruit, usually ripening about mid-August, with an attractive skin color;

(2) Its winter dormacy requirement approximates that of the well-known variety "Babcock," making it suited to culture in a subtropical climate;

(3) The stone of the fruit, when laid flat, is relatively rounder in outline as compared with other peach stones, and is pitted and furrowed sparsely with relatively deep pits and relatively shallow furrows; and (4) The flowers are exceptionally ornamental and large in size, and have as many as fourteen petals per flower.

These characteristics, in combination with the attractive color of the flowers, as hereinafter more fully described, their close arrangement on the stems, plus the fact that this new variety produces edible fruit of relatively high quality, makes the variety unique and different from any other flowering peaches now available in commerce, since the fruit of flowering peaches heretofore known, as a rule, is bitter and inedible, is of the clingstone type and very small, with rarely any skin color except green.

This new variety is distinct from its parents in that both parent varieties produce what is ordinarily considered as single flowers, whereas the new variety rarely has less than ten petals and often as many as fourteen petals. Also, the skin color of the fruit is more attractive and its flavor is more pleasing than the fruit of either parent.

Asexual reproduction of this new variety by budding at Ontario, California, shows that the foregoing characteristics come true to form and are established and transmitted through succeeding propagations.

The accompanying drawings show specimens of the flowers and fruit of the new variety, the fruit being shown in elevation and also in section both with and without the stone.

The following is a detained description of the new variety, based upon observations of specimens grown at Ontario, California, with color terminology in accordance with Robert F. Wilson's Horticultural Colour Chart, except where noted in relation to Ridgway's Colour Standards and Nomenclature:

Dates first and last picking: Ripens usually during second week of August. Picking period 10 days.

*Tree*

Medium size; moderately vigorous; upright; spreading; open; productive; regular bearer.

Trunk: Moderately stocky; moderately smooth.

Branches: Medium to stocky; medium smooth; dull.

*Color.*—Bark color on older branches and trunk is basically Russet, Plate XV (Ridgway) and streaked with Smoke Gray, Plate XLVI (Ridgway). Where fully exposed to sun, bark is almost entirely Russet, Plate XV (Ridgway). New branches are Pea Green, Plate 61/2, page 61; where exposed to sun they are Garnet Brown, Plate oo918/2, page 192.

*Lenticels.*—Numerous; small.

Leaves:

*Length.*—12 to 15 cm.

*Width.*—2½ to 3¼ cm. Medium size; acuminate; lanceolate; leathery.

*Color.*—Upper surface of leaf—near Deep Dull Yellow-Green (1), Plate XXXII (Ridgway). Lower surface of leaf—near Asphodel Green, Plate XLI (Ridgway).

*Leaf conformation.*—Usually quite crinkly along midrib.

*Margin.*—Glandular; finely serrate.

*Petiole.*—Medium length; 9 to 10 mm.; medium slender.

*Glands.*—Average number, 2 to 5. Usually alternate; medium size; reniform; position partly on petiole and partly on leaf base.

*Stipules.*—Early deciduous; 7 to 10 mm. long; narrow with pointed apex; long irregular glandular teeth on the margins.

Flower buds: Large; long; pointed.

*Bud.*—As it begins to show, color is near Spiraea Red, Plate o25, page 112, changing with maturity to become near Rhoda-

BEST AVAILABLE COPY mine Pink, Plate o27/1, page 138, just before the petals begin to unfold.

*Sepal.*—Non-adnate portions are tomentose on the outer surface, length 3 mm. The adnate portions forming the calyx are between Maroon, Plate I (Ridgeway), and Garnet Brown, Plate I (Ridgway) on the outer surface. Calyx inside near Mars Yellow, Plate III (Ridgway), as buds begin to unfold.

*Anther.*—Small, approximately 1 mm. in length. Anther while in the bud near Strawberry Pink, Plate I (Ridgway), in color around margins; central portion Pale Orange-Yellow, Plate III (Ridgway).

*Color of stamens.*—Near white as the bud unfolds, changing to near Rhodamine Pink, Plate 527/2, page 138, in the fully opened flower, changing to near Spiraea Red, Plate o25, page 112, in the basal portions, fading upward; the tip being near Spiraea Red, Plate o25/2, page 112, in the aged flowers.

Flower: Petalage, 12 to 14 with 1 to 4 petaloids. Petals arranged regularly in two or three rows, overlapping to give a solid form. Petals lie nearly flat but slightly cupped adaxilly, with the petaloids twisted and irregular in arrangement. 1 to 4 flowers borne at each node. The nodes are ½ to 1½ inches apart on the flowering branches. The flower diameter of a fully opened flower is 1⅜ to 1⅝ inches This size in combination with the flower number per node and length of node gives a nearly continuous spray of flowers along each flowering stem, making this variety exceptionally ornamental in appearance during the flowering season.

*Color of newly opened flower.*—Near Rhodamine Pink, Plate 527/2, page 138. As the flower ages it darkens in color in the center (the basal portion of the petals) to near Spiraea Red, Plate o25/1, page 112, the attachment region of the petal becoming as dark as Spiraea Red, Plate o25, page 112.

*Petal shape.*—Nearly oval, round at apical point, tapering on the basal end to form the attachment point. Outer petals entire, slightly cupped adaxilly. Inner petals sometimes entire, mostly crapelike giving an undulant margin. Petaloids very irregular.

*Petal measurements.*—Outer petal—usually 11 mm. wide at widest portion and 17 mm. long. Inner petal—usually 13 mm. wide at widest portion and 18 mm. long.

*Fruit*

Maturity when described—eating firm ripe Date—August 15, 1949.

Size: Variable; medium size. Diameter, axial, 2⅜ to 2¾ inches. Transverse in suture plane, 2⅛ to 2⅜ inches. At right angles to suture plane, 2⅛ to 2¼ inches.

Form: Uniform; slightly unsymmetrical; ovoid.

*Suture.*—An inconspicuous line; extends from base to apex; has slight depression beyond pistil point.

*Ventral surface.*—Rounded; slightly lipped throughout. Lips—equal to slightly unequal.

*Cavity.*—Flaring; rounded; elongated in suture plane with suture showing on one side. Depth—1.3 to 1.5 cm. Breadth—2 cm.

*Base.*—Rounded but somewhat truncate.

*Apex.*—Short; rounded. Pistil point—inconspicuous; apical.

Stem: Length, 6 to 8 mm. Medium stout; glabrous. Adherence to stone—moderate.

Skin: Medium thick; tough to medium; astringent; free from flesh. Tendency to crack—slight to none in dry weather.

*Color.*—Where shaded and near base near Mimosa Yellow, Plate 602/1, page 143. Otherwise highly colored with Delft Rose, Plate o20, page 108, darkening to near Oxblood Red, Plate oo823/3, page 191. Above color effects lightened by whitish down.

*Down.*—Abundant; medium length; does roll up when rubbed.

Flesh:

*Color.*—White. Surface of pit cavity—near Delft Rose, Plate o20/1, page 108.

*Juice.*—Moderately abundant.

*Texture.*—Firm; meaty.

*Fibres.*—Few; coarse; tender.

*Ripens.*—Evenly.

*Flavor.*—Somewhat austere.

*Aroma.*—Mild.

*Eating quality.*—Fair to good.

Stone: Free; parts from flesh smoothly.

*Size.*—Medium to small. Length—about 1⅛ inches. Breadth—about ⅞ inch. Thickness—about ⅝ inch.

*Form.*—Obovoid.

*Base.* — Straight. Hilum — broad; oval. Apex—cuspidate.

*Sides.* — Equal. Surface — ridged toward apex; pitted from base to above center.

*Ridges.*—Rounded.

*Pits.*—Circular, a few elongated. Ventral edge—thick; with wing throughout.

*Dorsal edge.*—Narrow with narrow groove to above center. Ridges on either side interrupted.

*Color of stone.*—Near Walnut Brown, Plate XXVIII (Ridgway).

*Tendency to split.*—None.

Use: Combination flowering ornamental tree and source of fresh fruit for the home garden.

Keeping quality: Good.

Shipping quality: Good to medium.

I claim:

A new and distinct variety of ornamental and fruiting peach tree, characterized as to novelty by its white-fleshed, freestone, edible fruit of relatively high quality and attractive color, by its relatively round stones pitted and furrowed sparsely with relatively deep pits and shallow furrows, by its winter dormancy requirement suitable to culture in subtropical climates, and by its exceptionally ornamental, many-petaled flowers of large size and attractive color, closely arranged on their stems, substantially as shown and described.

HERBERT C. SWIM.

No references cited.